United States Patent [19]

Iizuka et al.

[11] Patent Number: 5,837,526
[45] Date of Patent: Nov. 17, 1998

[54] BACILLUS STRAIN AND HARMFUL ORGANISM CONTROLLING AGENTS

[75] Inventors: Toshihiko Iizuka, Sapporo; Michito Tagawa, Shiraoka-machi; Satoshi Arai, Shiraoka-machi; Masatsugu Niizeki, Shiraoka-machi; Toshiro Miyake, Shiraoka-machi, all of Japan

[73] Assignee: Nissan Chemical Industries, Ltd., Tokyo, Japan

[21] Appl. No.: 880,684

[22] Filed: Jun. 23, 1997

Related U.S. Application Data

[62] Division of Ser. No. 542,921, Oct. 13, 1995.

[30] Foreign Application Priority Data

Oct. 14, 1994 [JP] Japan .................................. 6-276082

[51] Int. Cl.$^6$ ............................. C12N 1/00; C12N 15/32; A01H 5/00; A01H 5/10
[52] U.S. Cl. ................................. 435/252.3; 435/254.11; 435/419; 536/23.71; 800/205; 800/250
[58] Field of Search ...................... 536/23.71; 435/320.1, 435/419, 252.3, 254.11; 800/205, 250

[56] References Cited

FOREIGN PATENT DOCUMENTS

| 6-65292 | 3/1994 | Japan . |
| WO 93/03154 | 2/1993 | WIPO . |
| WO 94/05771 | 3/1994 | WIPO . |

OTHER PUBLICATIONS

Katsutoshi Ogiwara et al., "Nucleotide Sequence of the Gene Encoding Novel Delta–Endotoxin From Bacillus Thuringiensis Serovar Japonensis Strain Buibui Specific To Scarabaeid Beetles", Current Microbiology, vol. 30, No. 4, pp. 227–235, Apr. 1995.

*Primary Examiner*—Robert A. Wax
*Assistant Examiner*—Gabriele E. Bugaisky
*Attorney, Agent, or Firm*—Oblon, Spivak, McClelland, Maier & Neustadt, P.C.

[57] ABSTRACT

A novel crystal protein as an effective ingredient in harmful organism controlling agents, *Bacillus thuringiensis* var. *japonensis* strain N141 producing the protein, and a gene coding for the protein. This novel strain produces an insecticidal crystal toxin and is useful for a harmful organism controlling agent.

4 Claims, 3 Drawing Sheets

५,८३७,५२६

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3759 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Bacillus thuringiensis var. japonensis
        ( B ) STRAIN: N141

( i x ) FEATURE:
        ( A ) NAME/KEY: CDS
        ( B ) LOCATION: 47..3556

( x i ) SEQUENCE DESCRIPTION: SEQ ID NO:1:

```
TTTTAAATAC ATTGGAGTGT AATAGACTGG TATTGGAGGA ACAAGT ATG AAT CGA              55
                                                Met Asn Arg
                                                 1

AAT AAT CAA AAT GAA TAT GAA GTT ATT GAT GCC CCA CAT TGT GGG TGT           103
Asn Asn Gln Asn Glu Tyr Glu Val Ile Asp Ala Pro His Cys Gly Cys
      5              10                  15

CCG GCA GAT GAT GTT GTA AAA TAT CCT TTG ACA GAT GAT CCG AAT GCT           151
Pro Ala Asp Asp Val Val Lys Tyr Pro Leu Thr Asp Asp Pro Asn Ala
 20              25                  30                  35

GGA TTG CAA AAT ATG AAC TAT AAG GAA TAT TTA CAA ACG TAT GGT GGA           199
Gly Leu Gln Asn Met Asn Tyr Lys Glu Tyr Leu Gln Thr Tyr Gly Gly
             40                  45                  50

GAC TAT ACA GAT CCT CTT ATT AAT CCT AAC TTA TCT GTT AGT GGA AAA           247
Asp Tyr Thr Asp Pro Leu Ile Asn Pro Asn Leu Ser Val Ser Gly Lys
```

```
                          55                                      60                                      65
GAT  GTA  ATA  CAA  GTT  GGA  ATT  AAT  ATT  GTA  GGG  AGA  TTA  CTA  AGC  TTT        295
Asp  Val  Ile  Gln  Val  Gly  Ile  Asn  Ile  Val  Gly  Arg  Leu  Leu  Ser  Phe
          70                       75                       80

TTT  GGA  TTC  CCC  TTT  TCT  AGT  CAA  TGG  GTT  ACT  GTA  TAT  ACC  TAT  CTT        343
Phe  Gly  Phe  Pro  Phe  Ser  Ser  Gln  Trp  Val  Thr  Val  Tyr  Thr  Tyr  Leu
     85                            90                       95

TTA  AAC  AGC  TTG  TGG  CCG  GAT  GAC  GAG  AAT  TCT  GTA  TGG  GAC  GCT  TTT        391
Leu  Asn  Ser  Leu  Trp  Pro  Asp  Asp  Glu  Asn  Ser  Val  Trp  Asp  Ala  Phe
100                      105                      110                      115

ATG  GAG  AGA  GTA  GAA  GAA  CTT  ATT  GAT  CAA  AAA  ATC  TCA  GAA  GCA  GTA        439
Met  Glu  Arg  Val  Glu  Glu  Leu  Ile  Asp  Gln  Lys  Ile  Ser  Glu  Ala  Val
               120                      125                      130

AAG  GGT  AGG  GCA  TTG  GAT  GAC  CTA  ACT  GGA  TTA  CAA  TAT  AAT  TAT  AAT        487
Lys  Gly  Arg  Ala  Leu  Asp  Asp  Leu  Thr  Gly  Leu  Gln  Tyr  Asn  Tyr  Asn
          135                      140                      145

TTA  TAT  GTA  GAA  GCA  TTA  GAT  GAG  TGG  CTG  AAT  AGA  CCA  AAT  GGC  GCA        535
Leu  Tyr  Val  Glu  Ala  Leu  Asp  Glu  Trp  Leu  Asn  Arg  Pro  Asn  Gly  Ala
               150                      155                      160

AGG  GCA  TCC  TTA  GTT  TCT  CAG  CGA  TTT  AAC  ATT  TTA  GAT  AGC  CTA  TTT        583
Arg  Ala  Ser  Leu  Val  Ser  Gln  Arg  Phe  Asn  Ile  Leu  Asp  Ser  Leu  Phe
     165                           170                      175

ACA  CAA  TTT  ATG  CCA  AGC  TTT  GGC  TCT  GGT  CCT  GGA  AGT  CAA  AAT  TAT        631
Thr  Gln  Phe  Met  Pro  Ser  Phe  Gly  Ser  Gly  Pro  Gly  Ser  Gln  Asn  Tyr
180                      185                      190                      195

GCA  ACT  ATA  TTA  CTT  CCA  GTA  TAT  GCA  CAA  GCA  GCA  AAC  CTT  CAT  TTG        679
Ala  Thr  Ile  Leu  Leu  Pro  Val  Tyr  Ala  Gln  Ala  Ala  Asn  Leu  His  Leu
                    200                      205                      210

TTA  TTA  TTA  AAA  GAT  GCA  GAC  ATT  TAT  GGA  GCT  AGA  TGG  GGG  CTG  AAT        727
Leu  Leu  Leu  Lys  Asp  Ala  Asp  Ile  Tyr  Gly  Ala  Arg  Trp  Gly  Leu  Asn
               215                      220                      225

CAA  ACT  CAA  ATA  GAT  CAA  TTC  CAT  TCT  CGT  CAA  CAA  AGC  CTT  ACT  CAG        775
Gln  Thr  Gln  Ile  Asp  Gln  Phe  His  Ser  Arg  Gln  Gln  Ser  Leu  Thr  Gln
          230                      235                      240

ACT  TAT  ACA  AAT  CAT  TGT  GTT  ACT  GCG  TAT  AAT  GAT  GGA  TTA  GCG  GAA        823
Thr  Tyr  Thr  Asn  His  Cys  Val  Thr  Ala  Tyr  Asn  Asp  Gly  Leu  Ala  Glu
     245                           250                      255

TTA  AGA  GGC  ACA  ACC  GCT  GAG  AGT  TGG  TTT  AAA  TAC  AAT  CAA  TAT  CGT        871
Leu  Arg  Gly  Thr  Thr  Ala  Glu  Ser  Trp  Phe  Lys  Tyr  Asn  Gln  Tyr  Arg
260                      265                      270                      275

AGA  GAA  ATG  ACT  TTG  ACG  GCA  ATG  GAT  TTA  GTG  GCA  TTA  TTC  CCA  TAT        919
Arg  Glu  Met  Thr  Leu  Thr  Ala  Met  Asp  Leu  Val  Ala  Leu  Phe  Pro  Tyr
                    280                      285                      290

TAT  AAT  TTA  CGA  CAA  TAT  CCA  GAT  GGG  ACA  AAT  CCT  CAA  CTT  ACA  CGT        967
Tyr  Asn  Leu  Arg  Gln  Tyr  Pro  Asp  Gly  Thr  Asn  Pro  Gln  Leu  Thr  Arg
               295                      300                      305

GAG  GTC  TAT  ACA  GAT  CCG  ATT  GCA  TTT  GAT  CCA  CTG  GAA  CAA  CCA  ACT        1015
Glu  Val  Tyr  Thr  Asp  Pro  Ile  Ala  Phe  Asp  Pro  Leu  Glu  Gln  Pro  Thr
     310                           315                      320

ACT  CAA  TTA  TGT  CGA  TCA  TGG  TAC  ATT  AAC  CCA  GCT  TTT  CGA  AAT  CAT        1063
Thr  Gln  Leu  Cys  Arg  Ser  Trp  Tyr  Ile  Asn  Pro  Ala  Phe  Arg  Asn  His
325                      330                      335

TTG  AAT  TTC  TCT  GTA  CTA  GAA  AAT  TCA  TTG  ATT  CGT  CCC  CCG  CAC  CTT        1111
Leu  Asn  Phe  Ser  Val  Leu  Glu  Asn  Ser  Leu  Ile  Arg  Pro  Pro  His  Leu
340                      345                      350                      355

TTT  GAA  AGG  TTA  AGT  AAT  TTG  CAA  ATT  TTA  GTT  AAT  TAC  CAA  ACA  AAC        1159
Phe  Glu  Arg  Leu  Ser  Asn  Leu  Gln  Ile  Leu  Val  Asn  Tyr  Gln  Thr  Asn
               360                      365                      370

GGT  AGC  GCT  TGG  CGT  GGG  TCA  AGG  GTA  AGA  TAC  CAT  TAT  TTG  CAT  AGT        1207
Gly  Ser  Ala  Trp  Arg  Gly  Ser  Arg  Val  Arg  Tyr  His  Tyr  Leu  His  Ser
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 375 |     |     |     |     | 380 |     |     |     |     | 385 |     |      |
| TCT | ATA | ATA | CAG | GAA | AAA | AGT | TAC | GGC | CTC | CTC | AGT | GAT | CCC | GTT | GGA | 1255 |
| Ser | Ile | Ile | Gln | Glu | Lys | Ser | Tyr | Gly | Leu | Leu | Ser | Asp | Pro | Val | Gly |      |
|     |     | 390 |     |     |     |     | 395 |     |     |     |     | 400 |     |     |     |      |
| GCT | AAT | ATC | AAT | GTT | CAA | AAT | AAT | GAT | ATT | TAT | CAG | ATT | ATT | TCG | CAG | 1303 |
| Ala | Asn | Ile | Asn | Val | Gln | Asn | Asn | Asp | Ile | Tyr | Gln | Ile | Ile | Ser | Gln |      |
|     | 405 |     |     |     |     | 410 |     |     |     |     | 415 |     |     |     |     |      |
| GTT | AGC | AAT | TTT | GCT | AGT | CCT | GTT | GGC | TCA | TCA | TAT | AGT | GTT | TGG | GAC | 1351 |
| Val | Ser | Asn | Phe | Ala | Ser | Pro | Val | Gly | Ser | Ser | Tyr | Ser | Val | Trp | Asp |      |
| 420 |     |     |     |     | 425 |     |     |     |     | 430 |     |     |     |     | 435 |      |
| ACT | AAC | TTT | TAT | TTG | AGT | TCA | GGA | CAA | GTA | AGT | GGG | ATT | TCA | GGA | TAT | 1399 |
| Thr | Asn | Phe | Tyr | Leu | Ser | Ser | Gly | Gln | Val | Ser | Gly | Ile | Ser | Gly | Tyr |      |
|     |     |     |     | 440 |     |     |     |     | 445 |     |     |     |     | 450 |     |      |
| ACA | CAG | CAA | GGT | ATA | CCA | GCA | GTT | TGT | CTT | CAA | CAA | CGA | AAT | TCA | ACT | 1447 |
| Thr | Gln | Gln | Gly | Ile | Pro | Ala | Val | Cys | Leu | Gln | Gln | Arg | Asn | Ser | Thr |      |
|     |     |     | 455 |     |     |     |     | 460 |     |     |     |     | 465 |     |     |      |
| GAT | GAG | TTA | CCA | AGC | TTA | AAT | CCG | GAA | GGA | GAT | ATC | ATT | AGA | AAT | TAT | 1495 |
| Asp | Glu | Leu | Pro | Ser | Leu | Asn | Pro | Glu | Gly | Asp | Ile | Ile | Arg | Asn | Tyr |      |
|     |     | 470 |     |     |     |     | 475 |     |     |     |     | 480 |     |     |     |      |
| AGT | CAT | AGG | TTA | TCT | CAT | ATA | ACC | CAA | TAT | CGT | TTT | CAA | GCA | ACT | CAA | 1543 |
| Ser | His | Arg | Leu | Ser | His | Ile | Thr | Gln | Tyr | Arg | Phe | Gln | Ala | Thr | Gln |      |
|     | 485 |     |     |     |     | 490 |     |     |     |     | 495 |     |     |     |     |      |
| AGT | GGT | AGT | CCA | TCA | ACT | GTT | AGC | GCA | AAT | TTA | CCT | ACT | TGT | GTA | TGG | 1591 |
| Ser | Gly | Ser | Pro | Ser | Thr | Val | Ser | Ala | Asn | Leu | Pro | Thr | Cys | Val | Trp |      |
| 500 |     |     |     |     | 505 |     |     |     |     | 510 |     |     |     |     | 515 |      |
| ACG | CAT | CGA | GAT | GTG | GAC | CTT | GAT | AAT | ACC | ATT | ACT | GCG | AAT | CAA | ATT | 1639 |
| Thr | His | Arg | Asp | Val | Asp | Leu | Asp | Asn | Thr | Ile | Thr | Ala | Asn | Gln | Ile |      |
|     |     |     |     | 520 |     |     |     |     | 525 |     |     |     |     | 530 |     |      |
| ACA | CAA | CTA | CCA | TTA | GTA | AAG | GCA | TAT | GAG | CTA | AGT | AGT | GGT | GCT | ACT | 1687 |
| Thr | Gln | Leu | Pro | Leu | Val | Lys | Ala | Tyr | Glu | Leu | Ser | Ser | Gly | Ala | Thr |      |
|     |     |     | 535 |     |     |     |     | 540 |     |     |     |     | 545 |     |     |      |
| GTC | GTG | AAA | GGT | CCA | GGA | TTC | ACA | GGA | GGA | GAT | GTA | ATC | CGA | AGA | ACA | 1735 |
| Val | Val | Lys | Gly | Pro | Gly | Phe | Thr | Gly | Gly | Asp | Val | Ile | Arg | Arg | Thr |      |
|     |     | 550 |     |     |     |     | 555 |     |     |     |     | 560 |     |     |     |      |
| AAT | ACT | GGT | GGA | TTC | GGA | GCA | ATA | AGG | GTG | TCG | GTC | ACT | GGA | CCG | CTA | 1783 |
| Asn | Thr | Gly | Gly | Phe | Gly | Ala | Ile | Arg | Val | Ser | Val | Thr | Gly | Pro | Leu |      |
|     | 565 |     |     |     |     | 570 |     |     |     |     | 575 |     |     |     |     |      |
| ACA | CAA | CGA | TAT | CGC | ATA | AGG | TTC | CGT | TAT | GCT | TCG | ACA | ATA | GAT | TTT | 1831 |
| Thr | Gln | Arg | Tyr | Arg | Ile | Arg | Phe | Arg | Tyr | Ala | Ser | Thr | Ile | Asp | Phe |      |
| 580 |     |     |     |     | 585 |     |     |     |     | 590 |     |     |     |     | 595 |      |
| GAT | TTC | TTT | GTA | ACA | CGT | GGA | GGA | ACT | ACT | ATA | AAT | AAT | TTT | AGA | TTT | 1879 |
| Asp | Phe | Phe | Val | Thr | Arg | Gly | Gly | Thr | Thr | Ile | Asn | Asn | Phe | Arg | Phe |      |
|     |     |     |     | 600 |     |     |     |     | 605 |     |     |     |     | 610 |     |      |
| ACA | CGT | ACA | ATG | AAC | AGG | GGA | CAG | GAA | TCA | AGA | TAT | GAA | TCC | TAT | CGT | 1927 |
| Thr | Arg | Thr | Met | Asn | Arg | Gly | Gln | Glu | Ser | Arg | Tyr | Glu | Ser | Tyr | Arg |      |
|     |     |     | 615 |     |     |     |     | 620 |     |     |     |     | 625 |     |     |      |
| ACT | GTA | GAG | TTT | ACA | ACT | CCT | TTT | AAC | TTT | ACA | CAA | AGT | CAA | GAT | ATA | 1975 |
| Thr | Val | Glu | Phe | Thr | Thr | Pro | Phe | Asn | Phe | Thr | Gln | Ser | Gln | Asp | Ile |      |
|     |     | 630 |     |     |     |     | 635 |     |     |     |     | 640 |     |     |     |      |
| ATT | CGA | ACA | TCT | ATC | CAG | GGA | CTT | AGT | GGA | AAT | GGG | GAA | GTA | TAC | CTT | 2023 |
| Ile | Arg | Thr | Ser | Ile | Gln | Gly | Leu | Ser | Gly | Asn | Gly | Glu | Val | Tyr | Leu |      |
|     | 645 |     |     |     |     | 650 |     |     |     |     | 655 |     |     |     |     |      |
| GAT | AGA | ATT | GAA | ATC | ATC | CCT | GTG | AAC | CCG | GCA | CGA | GAA | GCA | GAA | GAG | 2071 |
| Asp | Arg | Ile | Glu | Ile | Ile | Pro | Val | Asn | Pro | Ala | Arg | Glu | Ala | Glu | Glu |      |
| 660 |     |     |     |     | 665 |     |     |     |     | 670 |     |     |     |     | 675 |      |
| GAT | TTA | GAA | GCA | GCG | AAG | AAA | GCG | GCT | AGG | CAG | AAC | TTG | TTT | ACA | CGT | 2119 |
| Asp | Leu | Glu | Ala | Ala | Lys | Lys | Ala | Ala | Arg | Gln | Asn | Leu | Phe | Thr | Arg |      |
|     |     |     |     | 680 |     |     |     |     | 685 |     |     |     |     | 690 |     |      |
| ACA | AGG | GAC | GGA | TTA | CAG | GTA | AAT | GTG | ACA | GAT | TAT | CAA | GTG | GAC | CAA | 2167 |
| Thr | Arg | Asp | Gly | Leu | Gln | Val | Asn | Val | Thr | Asp | Tyr | Gln | Val | Asp | Gln |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 695 |     |     |     |     | 700 |     |     |     |     | 705 |     |      |
| GCG | GCA | AAT | TTA | GTG | TCA | TGC | TTA | TCC | GAT | GAA | CAA | TAT | GGG | CAT | GAC | 2215 |
| Ala | Ala | Asn | Leu | Val | Ser | Cys | Leu | Ser | Asp | Glu | Gln | Tyr | Gly | His | Asp |      |
|     |     | 710 |     |     |     | 715 |     |     |     |     | 720 |     |     |     |     |      |
| AAA | AAG | ATG | TTA | TTG | GAA | GCG | GTA | AGA | GCG | GCA | AAA | CGC | CTC | AGC | CGC | 2263 |
| Lys | Lys | Met | Leu | Leu | Glu | Ala | Val | Arg | Ala | Ala | Lys | Arg | Leu | Ser | Arg |      |
|     | 725 |     |     |     |     | 730 |     |     |     |     | 735 |     |     |     |     |      |
| GAA | CGC | AAC | TTA | CTT | CAA | GAT | CCA | GAT | TTT | AAT | ACA | ATC | AAT | AGT | ACA | 2311 |
| Glu | Arg | Asn | Leu | Leu | Gln | Asp | Pro | Asp | Phe | Asn | Thr | Ile | Asn | Ser | Thr |      |
| 740 |     |     |     |     | 745 |     |     |     |     | 750 |     |     |     |     | 755 |      |
| GAA | GAG | AAT | GGC | TGG | AAG | GCA | AGT | AAC | GGT | GTT | ACT | ATT | AGC | GAG | GGC | 2359 |
| Glu | Glu | Asn | Gly | Trp | Lys | Ala | Ser | Asn | Gly | Val | Thr | Ile | Ser | Glu | Gly |      |
|     |     |     |     | 760 |     |     |     |     | 765 |     |     |     |     | 770 |     |      |
| GGT | CCA | TTC | TTT | AAA | GGT | CGT | GCA | CTT | CAG | TTA | GCA | AGC | GCA | AGA | GAA | 2407 |
| Gly | Pro | Phe | Phe | Lys | Gly | Arg | Ala | Leu | Gln | Leu | Ala | Ser | Ala | Arg | Glu |      |
|     |     |     | 775 |     |     |     |     | 780 |     |     |     |     | 785 |     |     |      |
| AAT | TAT | CCA | ACA | TAC | ATT | TAT | CAA | AAA | GTA | GAT | GCA | TCG | GTG | TTA | AAG | 2455 |
| Asn | Tyr | Pro | Thr | Tyr | Ile | Tyr | Gln | Lys | Val | Asp | Ala | Ser | Val | Leu | Lys |      |
|     |     | 790 |     |     |     |     | 795 |     |     |     |     | 800 |     |     |     |      |
| CCT | TAT | ACA | CGC | TAT | AGA | CTG | GAT | GGG | TTC | GTG | AAG | AGT | AGT | CAA | GAT | 2503 |
| Pro | Tyr | Thr | Arg | Tyr | Arg | Leu | Asp | Gly | Phe | Val | Lys | Ser | Ser | Gln | Asp |      |
|     | 805 |     |     |     |     | 810 |     |     |     |     | 815 |     |     |     |     |      |
| TTA | GAA | ATT | GAT | CTC | ATT | CAC | TAT | CAT | AAA | GTC | CAT | CTT | GTG | AAA | AAT | 2551 |
| Leu | Glu | Ile | Asp | Leu | Ile | His | Tyr | His | Lys | Val | His | Leu | Val | Lys | Asn |      |
| 820 |     |     |     |     | 825 |     |     |     |     | 830 |     |     |     |     | 835 |      |
| GTA | CCA | GAT | AAT | TTA | GTA | TCC | GAT | ACT | TAC | TCG | GAT | GGT | TCT | TGC | AGT | 2599 |
| Val | Pro | Asp | Asn | Leu | Val | Ser | Asp | Thr | Tyr | Ser | Asp | Gly | Ser | Cys | Ser |      |
|     |     |     |     | 840 |     |     |     |     | 845 |     |     |     |     | 850 |     |      |
| GGA | ATG | AAT | CGA | TGT | GAG | GAA | CAA | CAG | ATG | GTA | AAT | GCG | CAA | CTG | GAA | 2647 |
| Gly | Met | Asn | Arg | Cys | Glu | Glu | Gln | Gln | Met | Val | Asn | Ala | Gln | Leu | Glu |      |
|     |     |     | 855 |     |     |     |     | 860 |     |     |     |     | 865 |     |     |      |
| ACA | GAA | CAT | CAT | CAT | CCG | ATG | GAT | TGC | TGT | GAA | GCG | GCT | CAA | ACA | CAT | 2695 |
| Thr | Glu | His | His | His | Pro | Met | Asp | Cys | Cys | Glu | Ala | Ala | Gln | Thr | His |      |
|     |     | 870 |     |     |     |     | 875 |     |     |     |     | 880 |     |     |     |      |
| GAG | TTT | TCT | TCC | TAT | ATT | AAT | ACA | GGG | GAT | CTA | AAT | GCA | AGT | GTA | GAT | 2743 |
| Glu | Phe | Ser | Ser | Tyr | Ile | Asn | Thr | Gly | Asp | Leu | Asn | Ala | Ser | Val | Asp |      |
|     | 885 |     |     |     |     | 890 |     |     |     |     | 895 |     |     |     |     |      |
| CAG | GGC | ATT | TGG | GTT | GTA | TTA | AAA | GTT | CGA | ACA | ACA | GAT | GGG | TAT | GCG | 2791 |
| Gln | Gly | Ile | Trp | Val | Val | Leu | Lys | Val | Arg | Thr | Thr | Asp | Gly | Tyr | Ala |      |
| 900 |     |     |     |     | 905 |     |     |     |     | 910 |     |     |     |     | 915 |      |
| ACG | TTA | GGA | AAT | CTT | GAA | TTG | GTA | GAG | GTT | GGG | CCA | TTA | TCG | GGT | GAA | 2839 |
| Thr | Leu | Gly | Asn | Leu | Glu | Leu | Val | Glu | Val | Gly | Pro | Leu | Ser | Gly | Glu |      |
|     |     |     |     | 920 |     |     |     |     | 925 |     |     |     |     | 930 |     |      |
| TCT | CTA | GAA | CGG | GAA | CAA | AGA | GAT | AAT | GCG | AAA | TGG | AAT | GCA | GAG | CTA | 2887 |
| Ser | Leu | Glu | Arg | Glu | Gln | Arg | Asp | Asn | Ala | Lys | Trp | Asn | Ala | Glu | Leu |      |
|     |     |     | 935 |     |     |     |     | 940 |     |     |     |     | 945 |     |     |      |
| GGA | AGA | AAA | CGT | GCA | GAA | ATA | GAT | CGT | GTG | TAT | TTA | GCT | GCG | AAA | CAA | 2935 |
| Gly | Arg | Lys | Arg | Ala | Glu | Ile | Asp | Arg | Val | Tyr | Leu | Ala | Ala | Lys | Gln |      |
|     |     | 950 |     |     |     |     | 955 |     |     |     |     | 960 |     |     |     |      |
| GCA | ATT | AAT | CAT | CTG | TTT | GTA | GAC | TAT | CAA | GAT | CAA | CAA | TTA | AAT | CCA | 2983 |
| Ala | Ile | Asn | His | Leu | Phe | Val | Asp | Tyr | Gln | Asp | Gln | Gln | Leu | Asn | Pro |      |
|     | 965 |     |     |     |     | 970 |     |     |     |     | 975 |     |     |     |     |      |
| GAA | ATT | GGG | CTA | GCA | GAA | ATT | AAT | GAA | GCT | TCA | AAT | CTT | GTA | GAG | TCA | 3031 |
| Glu | Ile | Gly | Leu | Ala | Glu | Ile | Asn | Glu | Ala | Ser | Asn | Leu | Val | Glu | Ser |      |
| 980 |     |     |     |     | 985 |     |     |     |     | 990 |     |     |     |     | 995 |      |
| ATT | TCG | GGT | GTA | TAT | AGT | GAT | ACA | CTA | TTA | CAG | ATT | CCT | GGG | ATT | AAC | 3079 |
| Ile | Ser | Gly | Val | Tyr | Ser | Asp | Thr | Leu | Leu | Gln | Ile | Pro | Gly | Ile | Asn |      |
|     |     |     |     | 1000|     |     |     |     | 1005|     |     |     |     | 1010|     |      |
| TAC | GAA | ATT | TAC | ACA | GAG | TTA | TCC | GAT | CGC | TTA | CAA | CAA | GCA | TCG | TAT | 3127 |
| Tyr | Glu | Ile | Tyr | Thr | Glu | Leu | Ser | Asp | Arg | Leu | Gln | Gln | Ala | Ser | Tyr |      |

|                                                        |      |
|--------------------------------------------------------|------|
| 1015                    1020                    1025   |      |
| CTG TAT ACG TCT CGA AAT GCG GTG CAA AAT GGA GAC TTT AAC AGT GGT | 3175 |
| Leu Tyr Thr Ser Arg Asn Ala Val Gln Asn Gly Asp Phe Asn Ser Gly |      |
|         1030                1035                1040            |      |
| CTA GAT AGT TGG AAT ACA ACT ACG GAT GCA TCG GTT CAG CAA GAT GGC | 3223 |
| Leu Asp Ser Trp Asn Thr Thr Thr Asp Ala Ser Val Gln Gln Asp Gly |      |
|     1045                1050                1055                |      |
| AAT ATG CAT TTC TTA GTT CTT TCG CAT TGG GAT GCA CAA GTT TCT CAA | 3271 |
| Asn Met His Phe Leu Val Leu Ser His Trp Asp Ala Gln Val Ser Gln |      |
| 1060                1065                1070                1075 |      |
| CAA TTG AGA GTA AAT CCG AAT TGT AAG TAT GTC TTA CGT GTG ACA GCA | 3319 |
| Gln Leu Arg Val Asn Pro Asn Cys Lys Tyr Val Leu Arg Val Thr Ala |      |
|             1080                1085                1090        |      |
| AGA AAA GTA GGA GGC GGA GAT GGA TAC GTC ACA ATC CGA GAT GGC GCT | 3367 |
| Arg Lys Val Gly Gly Gly Asp Gly Tyr Val Thr Ile Arg Asp Gly Ala |      |
|         1095                1100                1105            |      |
| CAT CAC CAA GAA ACT CTT ACA TTT AAT GCA TGT GAC TAC GAT GTA AAT | 3415 |
| His His Gln Glu Thr Leu Thr Phe Asn Ala Cys Asp Tyr Asp Val Asn |      |
|     1110                1115                1120                |      |
| GGT ACG TAT GTC AAT GAC AAT TCG TAT ATA ACA GAA GAA GTG GTA TTC | 3463 |
| Gly Thr Tyr Val Asn Asp Asn Ser Tyr Ile Thr Glu Glu Val Val Phe |      |
| 1125                1130                1135                    |      |
| TAC CCA GAG ACA AAA CAT ATG TGG GTA GAG GTG AGT GAA TCC GAA GGT | 3511 |
| Tyr Pro Glu Thr Lys His Met Trp Val Glu Val Ser Glu Ser Glu Gly |      |
| 1140                1145                1150                1155 |      |
| TCA TTC TAT ATA GAC AGT ATT GAG TTT ATT GAA ACA CAA GAG TAG     | 3556 |
| Ser Phe Tyr Ile Asp Ser Ile Glu Phe Ile Glu Thr Gln Glu *       |      |
|             1160                1165                1170        |      |
| AAGAGGGGA TCCTAACGTA TAGCAACTAT GAGAGGATAC TCCGTACAAA CAAAGATTAA | 3616 |
| AAAAAGGTAA AATGAATAGA ACCCCCTACT GGTAGAAGGT CTGGTAGGGG GTTCTTACAT | 3676 |
| GAAAAAATGT AGCTGTTTAC TAAGGTATAT AAAAAACAGC ATATTTGATA GAAAAAAATG | 3736 |
| AGTACCTTAT AAAGAAAGAA TTC                                        | 3759 |

( 2 ) INFORMATION FOR SEQ ID NO:2:

( i ) SEQUENCE CHARACTERISTICS:
        ( A ) LENGTH: 1169 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met Asn Arg Asn Asn Gln Asn Glu Tyr Glu Val Ile Asp Ala Pro His
 1               5                  10                  15

Cys Gly Cys Pro Ala Asp Asp Val Val Lys Tyr Pro Leu Thr Asp Asp
                20                  25                  30

Pro Asn Ala Gly Leu Gln Asn Met Asn Tyr Lys Glu Tyr Leu Gln Thr
            35                  40                  45

Tyr Gly Gly Asp Tyr Thr Asp Pro Leu Ile Asn Pro Asn Leu Ser Val
        50                  55                  60

Ser Gly Lys Asp Val Ile Gln Val Gly Ile Asn Ile Val Gly Arg Leu
 65                  70                  75                  80

Leu Ser Phe Phe Gly Phe Pro Phe Ser Gln Trp Val Thr Val Tyr
                85                  90                  95

Thr Tyr Leu Leu Asn Ser Leu Trp Pro Asp Asp Glu Asn Ser Val Trp
                100                 105                 110

Asp Ala Phe Met Glu Arg Val Glu Glu Leu Ile Asp Gln Lys Ile Ser

-continued

|     |     |     | 115 |     |     |     |     | 120 |     |     |     |     | 125 |     |     |
| --- | --- | --- | --- | --- | --- | --- | --- | --- | --- | --- | --- | --- | --- | --- | --- |

Glu Ala Val Lys Gly Arg Ala Leu Asp Asp Leu Thr Gly Leu Gln Tyr
130 135 140

Asn Tyr Asn Leu Tyr Val Glu Ala Leu Asp Glu Trp Leu Asn Arg Pro
145 150 155 160

Asn Gly Ala Arg Ala Ser Leu Val Ser Gln Arg Phe Asn Ile Leu Asp
165 170 175

Ser Leu Phe Thr Gln Phe Met Pro Ser Phe Gly Ser Gly Pro Gly Ser
180 185 190

Gln Asn Tyr Ala Thr Ile Leu Leu Pro Val Tyr Ala Gln Ala Ala Asn
195 200 205

Leu His Leu Leu Leu Leu Lys Asp Ala Asp Ile Tyr Gly Ala Arg Trp
210 215 220

Gly Leu Asn Gln Thr Gln Ile Asp Gln Phe His Ser Arg Gln Gln Ser
225 230 235 240

Leu Thr Gln Thr Tyr Thr Asn His Cys Val Thr Ala Tyr Asn Asp Gly
245 250 255

Leu Ala Glu Leu Arg Gly Thr Thr Ala Glu Ser Trp Phe Lys Tyr Asn
260 265 270

Gln Tyr Arg Arg Glu Met Thr Leu Thr Ala Met Asp Leu Val Ala Leu
275 280 285

Phe Pro Tyr Tyr Asn Leu Arg Gln Tyr Pro Asp Gly Thr Asn Pro Gln
290 295 300

Leu Thr Arg Glu Val Tyr Thr Asp Pro Ile Ala Phe Asp Pro Leu Glu
305 310 315 320

Gln Pro Thr Thr Gln Leu Cys Arg Ser Trp Tyr Ile Asn Pro Ala Phe
325 330 335

Arg Asn His Leu Asn Phe Ser Val Leu Glu Asn Ser Leu Ile Arg Pro
340 345 350

Pro His Leu Phe Glu Arg Leu Ser Asn Leu Gln Ile Leu Val Asn Tyr
355 360 365

Gln Thr Asn Gly Ser Ala Trp Arg Gly Ser Arg Val Arg Tyr His Tyr
370 375 380

Leu His Ser Ser Ile Ile Gln Glu Lys Ser Tyr Gly Leu Leu Ser Asp
385 390 395 400

Pro Val Gly Ala Asn Ile Asn Val Gln Asn Asn Asp Ile Tyr Gln Ile
405 410 415

Ile Ser Gln Val Ser Asn Phe Ala Ser Pro Val Gly Ser Ser Tyr Ser
420 425 430

Val Trp Asp Thr Asn Phe Tyr Leu Ser Ser Gly Gln Val Ser Gly Ile
435 440 445

Ser Gly Tyr Thr Gln Gln Gly Ile Pro Ala Val Cys Leu Gln Gln Arg
450 455 460

Asn Ser Thr Asp Glu Leu Pro Ser Leu Asn Pro Glu Gly Asp Ile Ile
465 470 475 480

Arg Asn Tyr Ser His Arg Leu Ser His Ile Thr Gln Tyr Arg Phe Gln
485 490 495

Ala Thr Gln Ser Gly Ser Pro Ser Thr Val Ser Ala Asn Leu Pro Thr
500 505 510

Cys Val Trp Thr His Arg Asp Val Asp Leu Asp Asn Thr Ile Thr Ala
515 520 525

Asn Gln Ile Thr Gln Leu Pro Leu Val Lys Ala Tyr Glu Leu Ser Ser
530 535 540

```
Gly  Ala  Thr  Val  Val  Lys  Gly  Pro  Gly  Phe  Thr  Gly  Gly  Asp  Val  Ile
545                      550                 555                      560

Arg  Arg  Thr  Asn  Thr  Gly  Gly  Phe  Gly  Ala  Ile  Arg  Val  Ser  Val  Thr
                    565                 570                      575

Gly  Pro  Leu  Thr  Gln  Arg  Tyr  Arg  Ile  Arg  Phe  Arg  Tyr  Ala  Ser  Thr
               580                 585                      590

Ile  Asp  Phe  Asp  Phe  Phe  Val  Thr  Arg  Gly  Gly  Thr  Thr  Ile  Asn  Asn
               595                 600                 605

Phe  Arg  Phe  Thr  Arg  Thr  Met  Asn  Arg  Gly  Gln  Glu  Ser  Arg  Tyr  Glu
     610                      615                 620

Ser  Tyr  Arg  Thr  Val  Glu  Phe  Thr  Thr  Pro  Phe  Asn  Phe  Thr  Gln  Ser
625                      630                      635                      640

Gln  Asp  Ile  Ile  Arg  Thr  Ser  Ile  Gln  Gly  Leu  Ser  Gly  Asn  Gly  Glu
                    645                      650                      655

Val  Tyr  Leu  Asp  Arg  Ile  Glu  Ile  Ile  Pro  Val  Asn  Pro  Ala  Arg  Glu
               660                      665                      670

Ala  Glu  Glu  Asp  Leu  Glu  Ala  Ala  Lys  Lys  Ala  Ala  Arg  Gln  Asn  Leu
               675                      680                      685

Phe  Thr  Arg  Thr  Arg  Asp  Gly  Leu  Gln  Val  Asn  Val  Thr  Asp  Tyr  Gln
     690                      695                      700

Val  Asp  Gln  Ala  Ala  Asn  Leu  Val  Ser  Cys  Leu  Ser  Asp  Glu  Gln  Tyr
705                      710                      715                      720

Gly  His  Asp  Lys  Lys  Met  Leu  Leu  Glu  Ala  Val  Arg  Ala  Ala  Lys  Arg
                    725                      730                      735

Leu  Ser  Arg  Glu  Arg  Asn  Leu  Leu  Gln  Asp  Pro  Asp  Phe  Asn  Thr  Ile
               740                      745                      750

Asn  Ser  Thr  Glu  Glu  Asn  Gly  Trp  Lys  Ala  Ser  Asn  Gly  Val  Thr  Ile
          755                      760                      765

Ser  Glu  Gly  Gly  Pro  Phe  Phe  Lys  Gly  Arg  Ala  Leu  Gln  Leu  Ala  Ser
770                           775                      780

Ala  Arg  Glu  Asn  Tyr  Pro  Thr  Tyr  Ile  Tyr  Gln  Lys  Val  Asp  Ala  Ser
785                      790                      795                      800

Val  Leu  Lys  Pro  Tyr  Thr  Arg  Tyr  Arg  Leu  Asp  Gly  Phe  Val  Lys  Ser
                    805                      810                      815

Ser  Gln  Asp  Leu  Glu  Ile  Asp  Leu  Ile  His  Tyr  His  Lys  Val  His  Leu
               820                      825                      830

Val  Lys  Asn  Val  Pro  Asp  Asn  Leu  Val  Ser  Asp  Thr  Tyr  Ser  Asp  Gly
          835                      840                      845

Ser  Cys  Ser  Gly  Met  Asn  Arg  Cys  Glu  Glu  Gln  Met  Val  Asn  Ala
     850                      855                 860

Gln  Leu  Glu  Thr  Glu  His  His  His  Pro  Met  Asp  Cys  Cys  Glu  Ala  Ala
865                      870                      875                      880

Gln  Thr  His  Glu  Phe  Ser  Ser  Tyr  Ile  Asn  Thr  Gly  Asp  Leu  Asn  Ala
               885                      890                      895

Ser  Val  Asp  Gln  Gly  Ile  Trp  Val  Val  Leu  Lys  Val  Arg  Thr  Thr  Asp
               900                 905                      910

Gly  Tyr  Ala  Thr  Leu  Gly  Asn  Leu  Glu  Leu  Val  Glu  Val  Gly  Pro  Leu
          915                 920                      925

Ser  Gly  Glu  Ser  Leu  Glu  Arg  Glu  Gln  Arg  Asp  Asn  Ala  Lys  Trp  Asn
     930                      935                      940

Ala  Glu  Leu  Gly  Arg  Lys  Arg  Ala  Glu  Ile  Asp  Arg  Val  Tyr  Leu  Ala
945                      950                      955                      960

Ala  Lys  Gln  Ala  Ile  Asn  His  Leu  Phe  Val  Asp  Tyr  Gln  Asp  Gln  Gln
                    965                      970                      975
```

-continued

Leu Asn Pro Glu Ile Gly Leu Ala Glu Ile Asn Glu Ala Ser Asn Leu
980 985 990

Val Glu Ser Ile Ser Gly Val Tyr Ser Asp Thr Leu Leu Gln Ile Pro
995 1000 1005

Gly Ile Asn Tyr Glu Ile Tyr Thr Glu Leu Ser Asp Arg Leu Gln Gln
1010 1015 1020

Ala Ser Tyr Leu Tyr Thr Ser Arg Asn Ala Val Gln Asn Gly Asp Phe
1025 1030 1035 1040

Asn Ser Gly Leu Asp Ser Trp Asn Thr Thr Thr Asp Ala Ser Val Gln
1045 1050 1055

Gln Asp Gly Asn Met His Phe Leu Val Leu Ser His Trp Asp Ala Gln
1060 1065 1070

Val Ser Gln Gln Leu Arg Val Asn Pro Asn Cys Lys Tyr Val Leu Arg
1075 1080 1085

Val Thr Ala Arg Lys Val Gly Gly Gly Asp Gly Tyr Val Thr Ile Arg
1090 1095 1100

Asp Gly Ala His His Gln Glu Thr Leu Thr Phe Asn Ala Cys Asp Tyr
1105 1110 1115 1120

Asp Val Asn Gly Thr Tyr Val Asn Asp Asn Ser Tyr Ile Thr Glu Glu
1125 1130 1135

Val Val Phe Tyr Pro Glu Thr Lys His Met Trp Val Glu Val Ser Glu
1140 1145 1150

Ser Glu Gly Ser Phe Tyr Ile Asp Ser Ile Glu Phe Ile Glu Thr Gln
1155 1160 1165

Glu *
1170

BACILLUS STRAIN AND HARMFUL ORGANISM CONTROLLING AGENTS

This is a division of application Ser. No. 08/542,921, filed Oct. 13, 1995.

FIELD OF THE INVENTION

The present invention relates to novel *Bacillus thuringiensis* var. *japonensis* strain N141, hereinafter sometimes abbreviated as N141, an insecticidal crystal protein produced thereby, a gene coding for the protein, and a harmful organism controlling agent comprising the protein.

BACKGROUND OF THE INVENTION

*Bacillus thuringiensis*, hereinafter abbreviated as Bt, and crystalline toxic proteins produced thereby are very useful as microbial pesticides, which do not pollute the environment (Bt agents), particularly as insecticides against lepidopterous insect pests, and in practice have been widely used in the world.

Bt is a gram-positive bacilliform bacterium which produces a crystal protein at the sporulation stage in the end of the logarithmic growth phase. When orally taken into the mid-gut of an insect, the crystal protein will be subjected to alkaline and enzymatic activation in the digestive juice to show insecticidal activities accompanied with paralyses. However, the protein does not show any toxicity to mammals. The crystal proteins produced by Bt are generally of so-called diamond-shaped, bipyramidal or rhomboidal form. These crystal proteins are formed with endospores in the sporangium and released from the sporangium together with the endospores (Hannay, C. L.; Nature, 172, 1004 (1953)).

Bt has been classified on the basis of H-antigen according to the proposal by De Barjac and Bonefoi (Entomophaga, 7, 5–31 (1962)). A large number of subspecies have been found up to now.

The insecticidal activities of these strains are highly specific and may vary with subspecies. For example, it has been known that the subspecies *kurustaki* and *aizawai* show activities against lepidopterous insects while other subspecies *tenebrionis* and *japonensis buibui* are active against coleopterous insects.

In practice, however, each of strains belonging to the same subspecies has a different insecticidal activity spectrum. Some of lepidopterous pests may have acquired resistance to the Bt strain which showed an activity against the lepidopterous pests. Further, few strains have been reported which show an effective activity against coleopterous insects.

Thus, novel Bt agents would be desirable which are also effective against the lepidopterous pests having resistance to some known Bt agents. Also, there is a need for Bt agents having an activity against coleopterous insects.

SUMMARY OF THE INVENTION

The present inventors have found a novel strain producing a crystalline protein which has an excellent insecticidal activity against lepidopterous and coleopterous insects and attained the present invention.

Accordingly, the present invention is concerned with a novel strain N141 of *Bacillus thuringiensis* var. *japonensis* which has been originally deposited at National Institute of Bioscience and Human-Technology (NIBH), Agency of Industrial Science and Technology, Ministry of International Trade and Industry, Tsukuba, Japan on Oct. 6, 1994 under Accession Number FERM P-14576. This strain has been transferred to the deposit under Budapest Treaty conditions on Sep. 25, 1995 under Accession Number FERM BP-5241.

According to another aspect of the present invention, there is provided a harmful organism controlling agent comprising as a main ingredient an insecticidal crystal protein produced by N141, hereinafter abbreviated as N141 crystal protein. Further, the present invention provides a method of protecting a plant from damage caused by a pest which comprises applying the pest with the N141 crystal protein.

DESCRIPTION OF THE INVENTION

The novel strain N141 was isolated by a conventional method for isolating a bacterium of the genus Bacillus forming thermostable spores. Namely, a suspension of soil taken in Saitama, Japan was subjected to heat treatment at 50° to 90° C. and cultivated in a standard plating medium such as NB plate media to isolate the strain.

Features of the Novel Strain N141

Colony formation: An opaque white colony with an irregular border.

Cell morphology in the growth phase: Typical of Bt.

Serotype of H-antigen: 23, *japonensis*.

Figure 1:
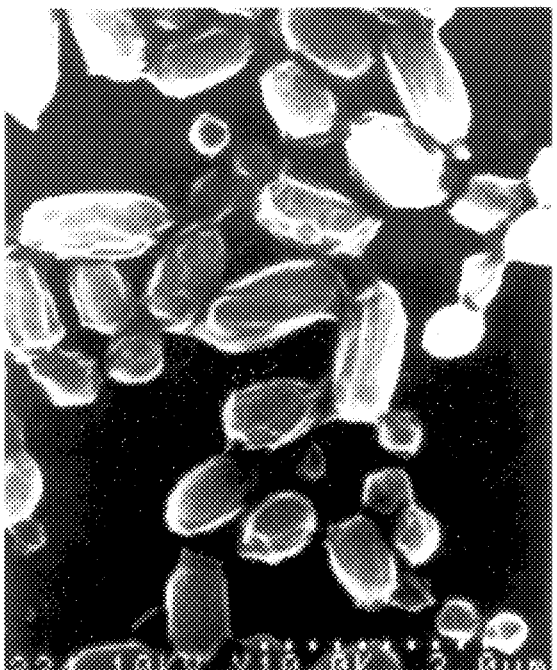
FIG. 1 is an electron microscopic photograph of *Bacillus thuringiensis* var. *japonensis* strain N141.

Intracellular component: A sporulating cell produces an amorphous crystal protein. The electron microscopic photograph of the crystal protein is shown in FIG. 1.

Alkali-soluble protein: This strain has a protein which runs to about 130,000 daltons on electrophoresis.

Activity: This strain has an insecticidal activity against lepidopterous and coleopterous pests tested.

Figure 2:
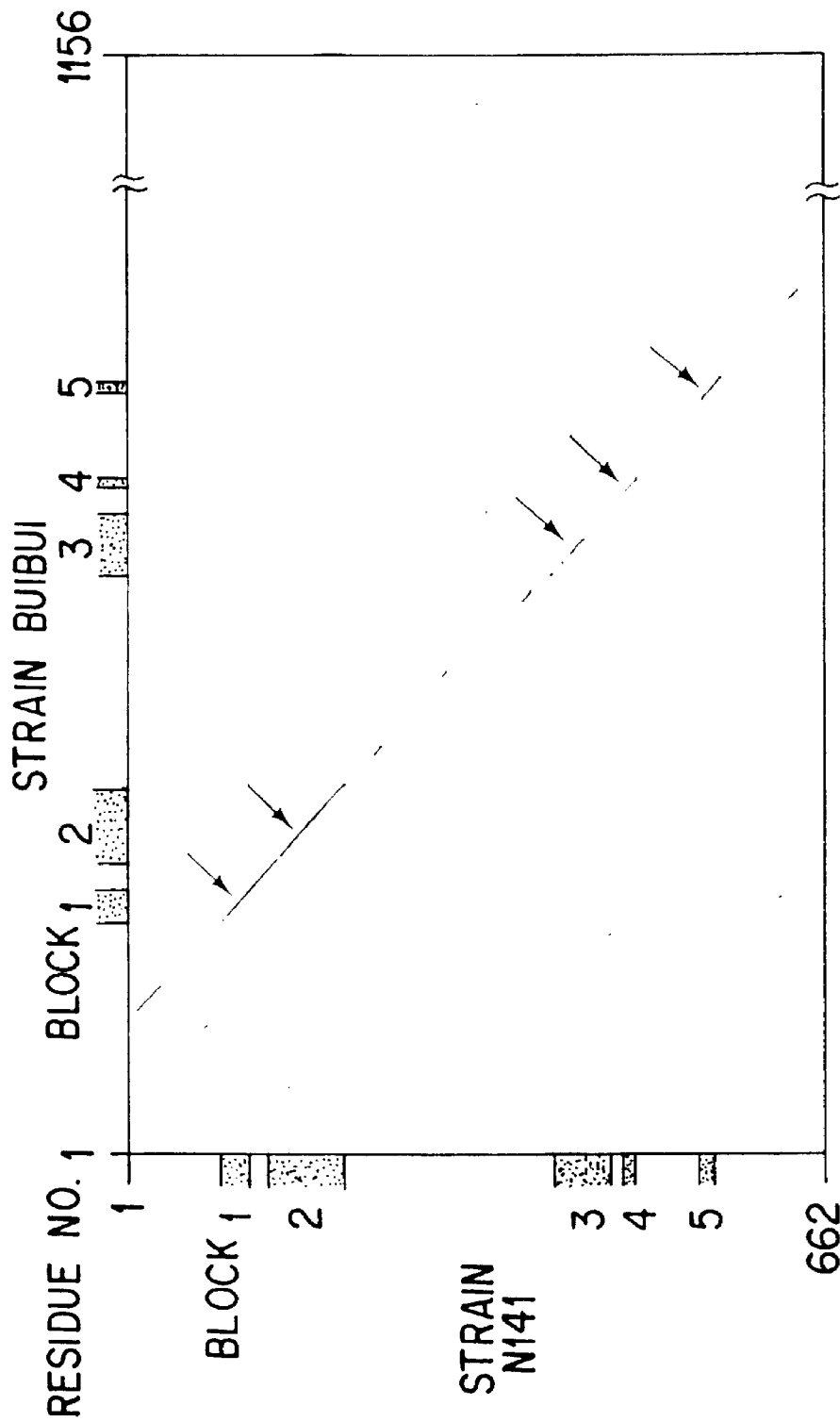
FIG. 2 shows a comparison of homology between the N-terminal 662 amino acids encoded by *Bacillus thuringiensis* var. *japonensis* N141 gene and the amino acid sequence encoded by *Bacillus thuringiensis buibui* gene.

Gene: Using antibodies raised by immunizing guinea pig with the crystal protein of about 130,000 daltons produced by this strain, screening was effected to clone a gene coding for the N141 crystal protein, hereinafter abbreviated as N141 gene. This gene has 3,759 bases and contains a translational region in from 47 to 3,556. Further, as compared with the known *japonensis buibui* gene having an activity against: coleopterous insects (Japanese Patent Application Laying-open No. 65292/1994), this gene has only about 60% of homology in the amino acid sequence level with the known gene as shown in FIG. 2.

From these, the N141 of the present invention is distinguished from known strains and therefore is novel.

N141 strain may be cultivated using known standard media and fermentation methods. Carbon sources may include sucrose, maltose, glucose, fructose, molasses and soluble starch.

Nitrogen sources may include ammonium sulfate, ammonium chloride, cottonseed powder, yeast extract, soybean cake and casein hydrolysate. Minerals and vitamins may be supplied from organic carbon sources or nitrogen sources, such as molasses and yeast extract, and optionally inorganic salts and vitamins may be further added. The cultivation may preferably be carried out at a pH of 5 to 8 and a temperature of 25° to 30° C. for 2 to 5 days in a stirred and aerated system under aerobic conditions.

After cultivation, the insecticidal crystal protein may be isolated from the culture medium in a conventional manner such as centrifugation or filtration.

The N141 crystal protein may be employed as an active ingredient in a harmful organism controlling agent for use in controlling coleopterous and lepidopterous insects. However, the N141 strain itself may also be employed as a crystal toxin-containing ingredient without isolation of the crystalline protein.

When the crystal toxin-containing ingredient is used in a harmful organism controlling agent, it may generally be mixed with a suitable carrier, including a natural mineral fiber such as talc or kaolin, a solid carrier such as diatomaceous earth, or a liquid carrier such as water, and optionally an emulsifier, dispersant, suspending agent, penetrant, spreader and/or stabilizer may be added to formulate into any practical dosage form such as wettable powder, dust, granule or flowable agent.

Optionally, the agent may be formulated or sprayed together with other herbicide, pesticide, fungicide, plant growth-regulatior, synergist, attractant, plant nutrient and/or fertilizer so long as they do not interfere with the crystalline toxin.

According to the present invention, the amount of the crystal toxin-containing ingredient applied may vary depending upon an application site, time and method, a pest to be controlled, and a crop to be protected; however, the amount of effective ingredient applied may usually about 0.1 to 99% by weight, preferably about 0.5 to 50% by weight of the agent.

Amounts of various ingredients in the agent of the present invention are exemplified below:

|  | Effective ingredient | Carrier | Surfactant | Auxiliary ingredients |
|---|---|---|---|---|
| Wettable powder | 1–70 | 15–93 | 3–10 | 0–5 |
| Dust | 0.01–30 | 67–99.5 |  | 0–3 |
| Granule | 0.01–30 | 67–99.5 |  | 0–8 |
| Flowable agent | 1–70 | 10–90 | 1–20 | 0–10 |

All the amounts shown in the above Table are % by weight.

When applied, a wettable powder or flowable agent is diluted with a predetermined amount of water before spraying while a dust or granule is directly sprayed without dilution with water.

Examples of each ingredient used in the agent may be as follows:

| (Wettable powder) | |
|---|---|
| Effective ingredient: | the crystal toxin-containing material according to the present invention; |
| Carrier: | calcium carbonate, kaolinite, Zeeklite D, Zeeklite PEP, diatomaceous earth, talc; |
| Surfactant: | Sorpol, calcium lignin sulfonate, Lunox; |
| Other ingredients: | Carplex #80. |
| (Dust) | |
| Effective ingredient: | the crystal toxin-containing material according to the present invention; |
| Carrier: | calcium carbonate, kaolinite, Zeeklite D, diatomaceous earth, talc; |

| -continued | |
|---|---|
| Other ingredients: | diisopropyl phosphate, Carplex #80. |
| (Granule) | |
| Effective ingredient: | the crystal toxin-containing material according to the present invention; |
| Carrier: | wheat flour, wheat bran, corn grits, Zeeklite D, |
| Other ingredients: | paraffin, soybean oil. |
| (Flowable agent) | |
| Effective ingredient: | the crystal toxin-containing material according to the present invention; |
| Carrier: | water; |
| Surfactant: | Sorpol, sodium lignin sulfonate, Lunox, Nippol; |
| Other ingredients: | ethylene glycol, propylene glycol. |

Formulation examples of the harmful organism controlling agent comprising the crystal toxin-containing material according to the present invention as an effective ingredient are given below but the present invention is not limited thereto. All parts are by weight.

| Formulation Example 1: Wettable powder | |
|---|---|
| crystal toxin-containing material according to the present invention | 25 parts |
| Zeeklite PEP (mixture of kaolinite and sericite; Zeeklite Industry Co.; trade name) | 66 parts |
| Sorpol 5039 (anionic surfactant; Toho Chemical Co.; trade name) | 4 parts |
| Carplex # 80 (white carbon; Shionogi Pharmaceutical Co.; trade name) | 3 parts |
| Calcium lignin sulfonate | 2 parts |
| The above ingredients are homogeneously mixed and pulverized to yield a wettable powder. | |

Upon application, the wettable powder is diluted 500 to 2,000 times and sprayed so that the amount of crystal toxin-containing ingredient applied is 0.1 to 5 kg per hectare.

| Formulation Example 2: Dust | |
|---|---|
| crystal toxin-containing material according to the present invention | 3.0 parts |
| clay | 95 parts |
| diisopropyl phosphate | 1.5 parts |
| Carplex # 80 (white carbon; Shionogi Pharmaceutical Co.; trade name) | 0.5 parts |

The above ingredients are homogeneously mixed and pulverized to yield a dust.

Upon application, the dust is sprayed so that the amount of crystal toxin-containing ingredient applied is 0.1 to 5 kg per hectare.

| Formulation Example 3: Flowable agent | |
|---|---|
| crystal toxin-containing material according to the present invention | 35 parts |
| Lunox 1000C (anionic surfactant; Toho Chemical Co.; trade name) | 0.5 parts |
| Sorpol 3353 (nonionic surfactant; Toho Chemical Co.; trade name) | 10 parts |
| 1% aqueous Xanthane gum solution (natural highpolymer) | 20 parts |
| water | 34.5 parts |

The above ingredients except the crystal toxin-containing ingredient of the present invention are homogeneously dissolved, mixed with the crystal toxin-containing material, thoroughly stirred and wet-pulverized in a sand mill to yield a flowable agent.

Upon application, the flowable agent is diluted 50 to 2,000 times and sprayed so that the amount of crystal toxin-containing ingredient applied is 0.1 to 5 kg per hectare.

The method of protecting a plant from damage caused by lepidopterous and/or coleopterous pests according to the present invention generally comprises treating, e.g., by spraying, a plant infected or suspected to be infected with the pest, with the harmful organism controlling agent diluted with a diluent such as water. The effective ingredient of the controlling agent is a toxic δ-endotoxin. If desired, the toxic δ-endotoxin may be applied in an isolated form separately from a bacterium producing the toxin to the plant or infectious pest. Generally, however, it is not necessary to isolate the crystalline protein from the bacterium.

Pests which may be destroyed by the method of the present invention include insects of the order Lepidoptera or Coleoptera.

Lepidopterous insects may include armyworms, such as common cutworm (*Spodoptera litura*), beat armyworm (*Spodoptera exigua*) and cabbage armyworm (*Mamestra brassicae*); diamondback moth (*Plutella xylostella*), rice leafroller (*Cnaphalocrocis medinalis*), rice stem borer (*Chilo suppressalis*), rice skipper (*Parnara guttata*), common white (*Pieris rapae crucivora*), oriental moth (*Monema flayescens*) and common yellow swallowtail (*Papilio machaon hippocrates*).

Coleopterous insects may include grubs, such as cupreous chafer (*Anomala cuprea*), *Anomala schonfeldti*, soybean beetle (*Anomala rufocuprea*), Asiatic garden beetle (*Maladera castanea*), chestnut brown chafer (*Adoretus tenuimaculatus*) and Japanese beetle (*Popillia japonica*); lady beetles, such as 28-spotted ladybird (*Epilachna vigintioctopunctata*) and large 28-spotted ladybird (*Epilachna viaintioctomaculata*); weevils, such as rice water weevil (*Lissorhoptrus oryzophilus*), *Scepticus griseus*, sweetpotato weevil (*Cylas formicarius*), hunting billbug (*Sphenophrus venatus vestius*) and maize weevil (*Sitophilus zeamaise*); leaf beetles, such as striped flea beetle (*Phyllotreta striolata*) and cucurbit leaf beetle (*Aulacophora femoralis*); click beetles, such as *Melanotus okinawaensis*; longicorn beetles, such as Japanese pine sawer (*Monochamus alternatus*) and sesame-spotted longicorn beetle (*Mesosa myops*); bark beetles, such as Japanese bark beetle (*Scolytus japonicus*) and alnus ambrosia beetle (*Xylosandrus germanus*); flour beetles, such as yellow mealworm (*Tenebrio molitor*) and red flour beetle (*Tribolium castaneum*).

The method of the present invention may be used to protect a wide variety of plants which are subject to infection with lepidopterous or coleopterous insect pests. The plants to be protected by the method of the present invention include vegetables such as cabbage and cauliflower, fruit trees such as citrus and apples, grains such as rice, wheat and beans, stored grains, stored foods, lawn in golf courses and gardens, industrial crops such as tea and sugarcane, as well as flower. Also, trees in non-crop lands such as parks and forests.

N141 gene may be isolated from N141 strain. The whole DNA of N141 strain may be digested with one or more restriction enzymes and the resulting DNA fragments may be size-fractionated into DNA fractions of 2 to 5 Kbp. The fractions may be ligated to a suitable vector and used to transform *Escherichia coli*. A transformed *E. coli* possessing a desired gene may be identified by enzyme immunoassay using antibodies against the N141 crystal protein.

The N141-derived crystal protein gene DNA thus identified may be treated with a suitable restriction enzyme and the resulting DNA fragment is ligated to a suitable cloning vector to make a gene cassette.

The gene cassette may be used to transform a microorganism, such as *E. coli*, and the base sequence of N141 crystal gene may then be determined by gene analysis methods such as dideoxy method.

Further, the gene cassette may also be used to transform a gram-positive bacterium having an insecticidal activity, such as Bt. Thus, a transformed Bt may be produced which is effective to control a wider variety of insects.

To express the N141 gene in a plant, a suitable restriction site may be introduced into both sides of each gene or a portion thereof in the gene cassette. This may be carried out by site-directed mutagenesis.

The portion of N141 gene coding for an insecticidally effective portion of N141 protein may be inserted into the nuclear genome of a single plant cell in a stable manner and the thus transformed cells may be used to produce a transformed plant which is resistant to insects.

The thus transformed plant may be used to produce transformed plants having the same properties, or the insecticidally effective portion of N141 gene may be introduced into other varieties of the same or related plant species. A seed produced from the transformed plant contains the insecticidally effective portion of N141 gene as a stable genome insert.

The N141 strain may further be transformed with a foreign Bt gene having one or more insecticidal activities, whereby a transformed N141 strain may be produced which is useful for destroying a wider variety of pests.

The N141 crystal protein may be used to immunize guinea pig to prepare an antibody specific to this crystal protein.

In the protected area, i.e., in the area to which N141 strain and/or N141 crystal protein has been applied, certain insects will ingest the N141 strain and/or N141 crystal protein or mixture thereof, or transformed plants and/or microorganisms incorporating the N141 gene, and as a result they are killed or injured by the N141 crystal protein.

EXAMPLES

The present invention will be further illustrated by the following examples but is not limited thereto.

Example 1

Isolation and Properties of N141 Strain

N141 strain was isolated from soil taken in Saitama, Japan.

Ten mg of a soil sample was placed in an Erlenmeyer flask and 10 mL of sterilized water was injected thereinto. The flask was shaken for 30 minutes and allowed to stand for some time. Two mL of the supernatant was taken out and immediately heated at 80° C. for 10 minutes. The heated solution was then diluted in two steps, 10 times and 100 times, respectively. Each solution (1 mL) of the ×10 and ×100 diluted solutions was incubated on an NB plating medium (8.4 g NUTRIENT BROTH, 20 g agar per liter of sterilized water) at 30° C. for 24 to 48 hours.

Features of the Novel Strain N141

Colony formation: An opaque white colony with an irregular border.

Cell morphology in the growth phase: Typical of Bt.

Serotype of H-antigen: 23, *japonensis*.

Intracellular component: A sporulating cell produces an amorphous crystal protein. The electron microscopic photograph of the crystal protein is shown in FIG. 1.

Alkali-soluble protein: This strain has a protein which runs to about 130,000 daltons on electrophoresis.

Activity: This strain has an insecticidal activity against lepidopterous and coleopterous pests tested.

Gene: Using antibodies raised by immunizing guinea pig with the crystal protein of about 130,000 daltons produced by this strain, screening was effected to clone a gene coding for the N141 crystal protein, hereinafter abbreviated as N141 gene. This gene has 3,759 bases and contains a translational region in from 47 to 3,556. Further, as compared with the known *japonensis buibui* gene having an activity against coleopterous insects (Japanese Patent Application Laying-open No. 65292/1994), this gene has only about 60% of homology in the amino acid sequence level with the known gene as shown in FIG. 2.

Example 2

Storage and Sterilization of N141 Strain

Desirably, for longtime storage of N141 strain, N141 is subjected to rotary shaking culture with NB liquid medium (8.4 g NUTRIENT BROTH per liter of sterilized water) at 30° C. and 150–200 rpm for 24 to 72 hours and equal amounts of the culture medium and 30% glycerol are mixed and stored at −80° C., or alternatively, said culture medium is centrifuged and the resulting cells are suspended in a protective liquid (10% skim milk, 1% sodium glutamate) and dried under vacuum.

Sterilization of N141 strain is carried out in an autoclave at 120° C. for 20 minutes.

Example 3

Purification of Crystal Protein of N141 Strain

A platinum loopful of N141 strain was inoculated in a test tube containing 5 mL of NB liquid medium (8.4 g NUTRIENT BROTH per liter of sterilized water) and reciprocal shaking culture was carried out at 30° C. for 12 to 24 hours to yield a seed culture. The seed culture was inoculated in a 500 mL Erlenmeyer flask containing 100 ml of NB liquid medium (8.4 g NUTRIENT BROTH per liter of sterilized water) in a final concentration of 1% and shaking culture was effected at 30° C. and 150 rpm for 72 to 96 hours. Thereafter, cells, spores and crystal proteins were collected by centrifugation. A suitable amount of buffer (Tris-HCl, NaCl, EDTA) was added to the resulting precipitate and the mixture was subjected to ultrasonication to yield a suspension.

Example 4

Properties of N141 Crystal Protein

The suspension obtained in Example 3 was subjected to electrophoresis on 8% SDS-PAGE gel to investigate an electrophoretic pattern. Also, western blotting analysis was carried out using antibodies. As a result, it was revealed that N141 strain produces a crystal protein with a molecular weight of about 130,000 daltons.

Example 5

Insecticidal Activity of N141 Strain Against Cupreous Chafer (*Anomala cuprea*)

The suspension prepared in Example 3 was diluted to a predetermined concentration and a spreader was added thereto. The thus prepared sample solution was mixed into leaf mould which had previously sterilized, and cupreous chafer (*Anomala cuprea*) was released. As a result of observation, an insecticidal activity against cupreous chafer (*Anomala cuprea*) was recognized.

Example 6

Insecticidal Activity of N141 Strain and N141 Crystal Protein Against Diamondback Moth (*Plutella xylostella*)

The suspension prepared in Example 3 was diluted to a predetermined concentration and a spreader was added thereto to prepare a sample solution. A leaf of cabbage was immersed into the sample solution, air-dried thoroughly and placed into a styrol cup containing a wet filter paper. Larvae of diamondback moth (*Plutella xylostella*) in the middle of 3 larval instars stage were released into the cup and a mortality after 6 days was calculated from the following equation. The test was performed in 5-plicate with 5 larvae in each zone.

$$\text{Mortality (\%)} = \frac{\text{the number of dead insects}}{\text{the total number of insects}} \times 100$$

The results are shown in Table 1.

TABLE 1

Insecticidal activity of N141 strain and N141 crystal protein against larvae of diamondback moth (*Plutella xylostella*) in the middle of 3 larval instars stage

| Concentration (ppm) | Mortality (%) |
|---|---|
| 10000 | 100 |
| 3000 | 100 |
| 1000 | 100 |
| 100 | 50 |

Example 7

Insecticidal Activity of N141 Strain and N141 Crystal Protein Against *Bombyx mori*

The suspension prepared in Example 3 was diluted to a predetermined concentration and a spreader was added thereto to prepare a sample solution. A leaf of mulberry was immersed into the sample solution, air-dried thoroughly and placed into a styrol cup containing a wet filter paper. Larvae of *Bombyx mori* on the second day of of 3 larval instars stage were released into the cup and a mortality after 6 days was calculated from the following equation. The test was performed in 5-plicate with 5 larvae in each zone.

$$\text{Mortality (\%)} = \frac{\text{the number of dead insects}}{\text{the total number of insects}} \times 100$$

The results are shown in Table 2.

TABLE 2

Insecticidal activity of N141 strain and N141 crystal protein against larvae of Bombyx mori on the second day of 3 larval instars stage

| Concentration (ppm) | Mortality (%) |
|---|---|
| 3000 | 100 |
| 1000 | 95 |
| 100 | 50 |

Example 8

Isolation of N141 Gene

The whole DNA was prepared from N141 strain and partially digested with EcoRI. The digested DNAs were fractionated and DNA fragments of about 2 to 5 Kbp were ligated to a phage vector λgt11 digested with EcoRI. These vectors were used to transform E. coli. The recombinant E. coli clones were screened with antibodies raised by immunizing guinea pig with about 130 kDa protein which was assumed to be N141 crystal protein, to identify clones containing N141 gene. DNAs were prepared from the identified recombinant E. coli clones and digested with restriction enzyme EcoRI. The digested DNA fragments were subjected to electrophoresis on 0.8% agarose gel to identify an inserted DNA fragment of about 3.4 Kbp.

Example 9

Cloning of N141 Gene

Figure 3:
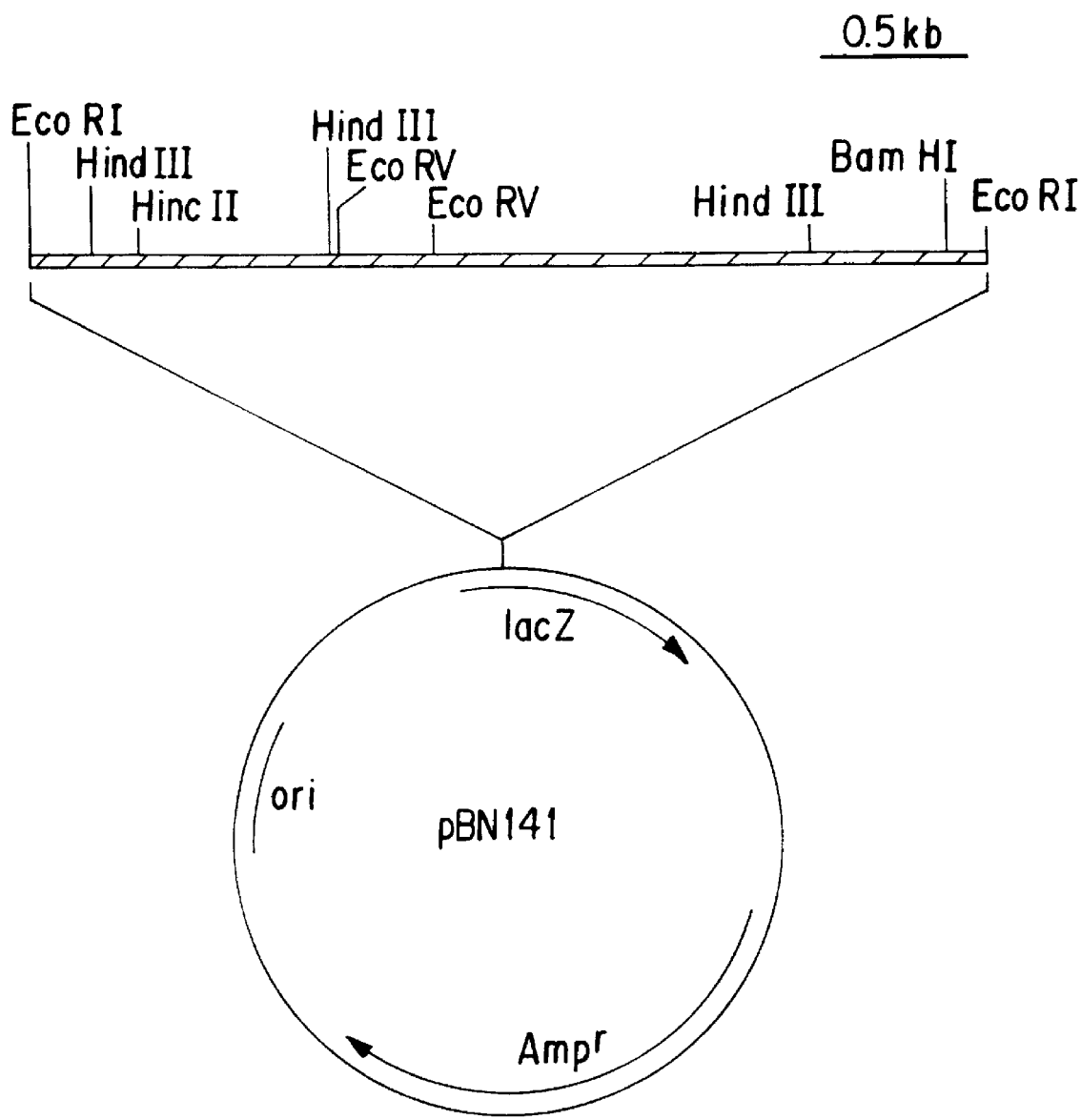
FIG. 3 depicts the cassette pBN141 comprising *Bacillus thuringiensis* var. *japonensis* N141 gene inserted into a vector.

The DNA fragments prepared in Example 8 were fractionated and ligated to a plasmid vector Bluescript II SK (−) digested with EcoRI so as to construct a gene cassette (pBN141; FIG. 3). This pBN141 was not of full length and cloning was again repeated. The base sequence of a DNA fragment containing a full length N141 gene was determined by the dideoxy method.

Example 10

Base and Amino Acid Sequences of N141 Gene

The base sequence consisted of 3759 bases as shown in SEQ ID NO:1. The open reading frame (ORF) consisted of 3510 bases, i.e. from 47th to 3556th bases, and coded for 1169 amino acids (the 1170th base being a termination codon). The amino acid sequence of the N-terminal 662 amino acids of this N141 protein was compared with those of a protein encoded by the known japonensis buibui gene which shows an activity against coleopterous insects (Japanese Patent Application Laying-open No. 65292/1994). It was found that the two genes had a homology in the amino acid level of only about 60% as shown in FIG. 2.

Example 11

Expression of N141 Crystal Protein in E. coli DH5α

To produce the crystal protein from N141 gene, the gene cassette pBN141 was used to transform E. coli DH5α. The resulting recombinant E. coli, hereinafter referred to E. coli:DH5α (pBN141), was incubated in LB-amp liquid medium (10 g Trypton, 10 g NaCl, 5 g Yeast extract, 0.2% glucose, 50 mg ampicillin per liter of sterilized water) at 37° C. for about 3 hours. IPTG was added to a final concentration of 1 mM and further incubated at 37° C. for 20 hours. After culture, the culture medium was centrifuged and 4 unit volumes of Lysis buffer were added to unit weight of the precipitate to suspend at room temperature for 10 hours. Then, Lysozyme was added and mixed in a final concentration of 1 mg/mL and allowed to stand on ice for 10 minutes. Further, Triton X-100 was added and mixed in a final concentration of 1% and allowed to stand at room temperature for 10 minutes. After centrifugation the supernatant was recovered.

Example 12

Properties of Protein Expressed in E. coli:DH5α (pBN141)

The supernatant obtained in Example 11 was subjected to electrophoresis on 8% SDS-PAGE gel and to western blotting using antibodies. As a result, it was confirmed that E. coli:DH5α (pBN141) produced N141 crystal protein.

Example 13

Insecticidal Activity of the Protein Expressed in E. coli:DH5α (pBN141) Against Larvae of Diamondback Moth (Plutella xylostella)

To the supernatant solution obtained in Example 11, a spreader was added and diluted to prepare a sample solution. A leaf of cabbage was immersed into the sample solution, air-dried thoroughly and placed into a styrol cup containing a wet filter paper. Larvae of diamondback moth (Plutella xylostella) in the middle of 3 larval instars stage were released into the cup and a mortality after 6 days was calculated from the following equation. The test was performed in 5-plicate with 5 larvae in each zone.

$$\text{Mortality (\%)} = \frac{\text{the number of dead insects}}{\text{the total number of insects}} \times 100$$

The results are shown in Table 3.

TABLE 3

Insecticidal activity of the protein expressed in E. coli:DH5α (pBN141) against larvae of diamondback moth (Plutella xylostella) in the middle of 3 larval instars stage

| Concentration (ppm) | Mortality (%) |
|---|---|
| 200 | 85 |
| 100 | 50 |

Example 14

Insecticidal Activity of the Protein Expressed in E. coli:DH5α (pBN141) Against Larvae of Bombyx mori To the supernatant solution obtained in Example 11, a spreader was added and diluted to prepare a sample solution. A leaf of mulberry was immersed into the sample solution, air-dried thoroughly and placed into a styrol cup containing a wet filter paper. Larvae of *Bombyx mori* on the second day of of 3 larval instars stage were released into the cup and a mortality after 6 days was calculated from the following equation. The test was performed in 5-plicate with 5 larvae in each zone.

$$\text{Mortality (\%)} = \frac{\text{the number of dead insects}}{\text{the total number of insects}} \times 100$$

The results are shown in Table 4.

TABLE 4

Insecticidal activity of the protein expressed in
*E. coli*:DH5α (pBN141) against larvae of *Bombyx mori*
on the second day of 3 larval instars stage

| Concentration (ppm) | Mortality (%) |
|---|---|
| 200 | 70 |

While the above examples are directed to only several embodiments of the present invention, it is apparent to those skilled in the art that many other modifications and/or changes are contemplated in the present invention. For example, any peptide having an insecticidal activity and coding for an amino acid sequence which is different from that represented by SEQ ID NO:2 in that one or more amino acids may be added, deleted and/or replaced, as well as any DNA coding for such a modified peptide are included within the scope of the present invention.

The N141 crystal protein of the present invention has an activity not only against lepidopterous insects but also coleopterous insects such as cupreous chafer (*Anomala cuprea*) and is expected to be useful for insecticidal compositions.

What is claimed is:

1. An isolated and substantially purified DNA coding for an insecticidal crystal protein produced by *Bacillus thuringiensis* var. *japonensis* strain N141 having the amino acid sequence of SEQ ID NO:2.

2. The DNA of claim 1, which has a base sequence represented by SEQ ID NO:1.

3. A microorganism transformed with the DNA of claim 1.

4. A plant or seed thereof transformed with the DNA of claim 1.

* * * * *